United States Patent [19]

de Jongh et al.

[11] Patent Number: 4,808,710
[45] Date of Patent: Feb. 28, 1989

[54] 18-PHENYLOESTRANE DERIVATIVES

[75] Inventors: Hendrik P. de Jongh, Oss; Martinus J. van den Heuvel, Vught, both of Netherlands

[73] Assignee: Akzo N.V., Arnhem, Netherlands

[21] Appl. No.: 74,442

[22] Filed: Jul. 16, 1987

[30] Foreign Application Priority Data

Jul. 23, 1986 [NL] Netherlands ............... 8601903

[51] Int. Cl.$^4$ ............... C07J 33/00; C07J 1/00
[52] U.S. Cl. .................. 540/30; 540/41; 260/397.4; 260/397.3; 260/397.5; 514/177; 514/178
[58] Field of Search .......... 260/397, 397.1, 397.3, 260/397.4, 397.45, 397.5; 514/177, 178; 540/41, 30

[56] References Cited

U.S. PATENT DOCUMENTS

| | | | |
|---|---|---|---|
| 1,255,345 | 12/1971 | Baran | 540/41 |
| 3,074,978 | 1/1963 | Nomine et al. | 260/397.5 |
| 3,100,204 | 9/1963 | Oberster et al. | 260/397.47 |
| 3,177,205 | 4/1965 | Bowers et al. | 260/397.47 |
| 3,494,942 | 2/1970 | Miki et al. | 260/397.5 |
| 3,725,439 | 4/1973 | Patchett et al. | 260/397.5 |
| 4,167,517 | 9/1979 | Ponsold et al. | 260/397.5 |
| 4,386,085 | 5/1983 | Teutsch et al. | 514/179 |
| 4,447,424 | 5/1984 | Teutsch et al. | 514/179 |
| 4,519,946 | 5/1985 | Teutsch et al. | 540/76 |
| 4,634,695 | 1/1987 | Torelli et al. | 514/178 |

OTHER PUBLICATIONS

Keana J. F. W., "Protection of Carbonyl & Hydroxyl Groups" in Steroid Reactions, (1963), Holden–Day, Inc., (U.S.A.), pp. 1–5, 30, 34, 35.

Chemical Abstracts, vol. 66, No. 5, Jan. 30, 1967, p. 1828, Item 18810m.
Chemical Abstracts, vol. 66, Oct. 31, 1967, Item 18820q.

Primary Examiner—H. M. S. Sneed
Assistant Examiner—J. Saba
Attorney, Agent, or Firm—William M. Blackstone

[57] ABSTRACT

A novel class of steroids having pregnancy-terminating and/or pregnancy-preventing activity and a very low antiglucocorticoid activity have been found. The compounds have the general formula:

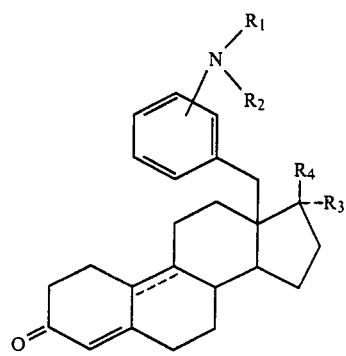

wherein $R_1$ and $R_2$ each separately represent H or a (1–4 C) hydrocarbon radical or together represent a (2–6 C) hydrocarbon radical, $R_3$ represents H or a (1–4 C) hydrocarbon radical, optionally having an OH substituent, $R_4$ represents OH or an ester or ether group, or together with $R_3$ represents O or a heterocyclic ring system containing O, and wherein the broken line indicates an optionally present double bond between the carbon atoms at positions 9 and 10 of the steroid skeleton.

4 Claims, No Drawings

18-PHENYLOESTRANE DERIVATIVES

The invention relates to novel 18-phenyloestrane derivatives, in particular to novel 18-phenyl-$\Delta^4$-oestren-3-one derivatives which are substituted in addition at the positions 17α and 17β. The invention also relates to processes for the preparation of these compounds and to pharmaceutical products which contain said derivatives as an active constituent.

Antiprogestatives are substances which have an affinity for the progesterone receptor, such substances not exercising, or exercising to a reduced extent, the action of progesterone. Progesterone is involved, inter alia, in the nidation of a fertilized egg cell in the wall of the uterus. It will be possible to prevent the nidation by occupying receptor points in the uterus cells with antiprogestatives, as a result of which the pregnancy can be terminated at a very early stage. Antiprogestatives are known from European Patent Application No. 0,057,115.

A novel group of compounds has now been found which have pregnancy-terminating and/or pregnancy-preventing activity, these being in particular novel 18-phenylsteroids from the oestrane series having the general formula:

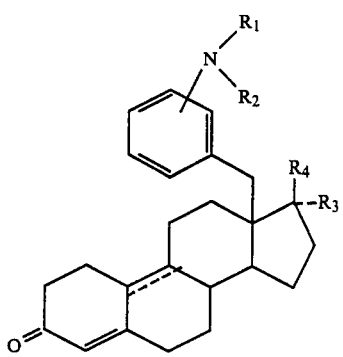

wherein $R_1$ and $R_2$ each separately represent H or a (1-4 C) hydrocarbon radical or together represent a hydrocarbon radical (2-6), $R_3$ represents H or a (1-4 C) hydrocarbon radical, optionally having an OH substituent, and $R_4$ represents OH or an ester or ether group or together with $R_3$ represents O or a heterocyclic ring system containing O, and wherein the broken line indicates an optionally present double bond between the carbon atoms at positions 9 and 10 of the steroid skeleton.

The (1-4 C) hydrocarbon group in $R_1$ and $R_2$ may be, inter alia, methyl, ethyl, vinyl, ethynyl, propyl, 2-propenyl, allenyl, 1-propynyl, butyl and branched analogues thereof. If $R_1$ and $R_2$ together form a hydrocarbon group containing 2-6 carbon atoms, the hydrocarbon group may be saturated or unsaturated. Preferably, the hydrocarbon group contains 4 or 5 carbon atoms. $R_1$ and $R_2$ preferably stand for a saturated alkyl group containing 1-3 carbon atoms, and even more preferably for methyl. The (1-4) hydrocarbon group in $R_3$ may be, inter alia, methyl, ethyl, vinyl, ethynyl, propyl, 2-propenyl, allenyl, 1-propynyl, butyl and analogues thereof which are branched and/or provided with an OH substituent such as, for example, 3-hydroxy-1-propynyl.

If $R_3$ together with $R_4$ does not represent O or a heterocyclic ring system containing O, $R_3$ is preferably an unsaturated hydrocarbon group containing 2 or 3 carbon atoms, optionally provided with an OH substituent.

The ester group optionally present at position 17 is preferably derived from an organic carboxylic acid containing 1–18 C atoms such as acetic acid, propionic acid, butyric acid, trimethylacetic acid, phenylacetic acid, cyclopentylpropionic acid, phenylpropionic acid, valeric acid, caproic acid, pelargonic acid, lauric acid, palmitic acid, benzoic acid or succinic acid.

The ether group optionally present at position 17 is preferably derived from an alkyl ether containing 1-12 C atoms such as, for example, methyl ethyl, ethyl ether, cyclopentyl ether or cyclohexenyl ether, or from an aromatic ether such as benzyl ether or from a heterocyclic ether such as tetrahydropyranyl ether. If $R_4$ does not represent O or—together with $R_3$—a heterocyclic ring system containing O, $R_4$ is preferably OH. If $R_3$ and $R_4$ together represent a heterocyclic ring system containing O, the preference is for ring systems containing 5 atoms in the ring and, in particular, for the ring systems in which the ring is bonded to position 17β of the steroid skeleton by means of an oxygen atom which forms part of the ring. The greatest preference is for the following heterocyclic ring systems:

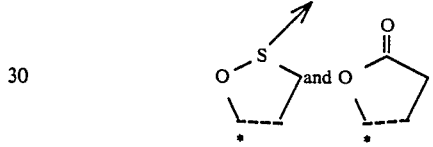

(The carbon atom which is provided with an * being the carbon atom at position 17 of the steroid skeleton).

The amino substituent on the phenyl group at position 18 may be bound to the ortho, meta or para position of the phenyl group. Preferably it is the meta or para position. The bond between the carbon atoms at position 9 and 10 may be a single or double bond.

The invention also relates to pharmaceutical compositions which contain one or more of the compounds according to the invention as an active ingredient. The novel compounds may be administered orally or parenterally in the usual manner, in combination with auxiliary pharmaceutical substances, in the form of tablets, pills, dragees and other usual dosage forms. The dosage forms can be prepared by known galenic procedures.

The compounds according to the invention can be prepared in a manner known per se.

Thus, starting from 3,17-dioxo-oestr-5-ene-18,11β-lactone 3,17-diethyleneacetal or another 3,17 di-acetal, the required aminophenyl group can be introduced by reaction with Grignard reagent which contains the aminophenyl group. In this reaction an OH group at 11 and a ketone group at 18 are also formed. To introduce a dimethylaminophenyl group, dimethylaminophenyl magnesium bromide may, for example, be used. The 18-one group is then completely reduced to form an 11β-hydroxy-18-aminophenyl-oestr-5-ene-3,17-dione-3,17-diethyleneacetal or another 3,17-di-acetal.

This compound may be used both for the preparation of compounds according to the invention with a double bond between the carbon atoms at position 9 and 10 of the steroid skeleton and for the preparatation of compounds according to the invention without said double bond.

To prepare compounds according to the invention without said double bond, the hydroxyl group at position 11 is first converted into the corresponding 11-ketone which is then completely reduced. The 18-aminophenyl-oestr-5-ene-3,17-dione 3,17-diethyleneacetal thus obtained is then deprotected by removal of the diethyleneacetal groups to form the 4-ene-3,17-dione. After protecting the ketone group at position 3 (for example, by means of etherification or acetalisation) the hydrocarbon group at position 17α can be introduced with the simultaneous formation of the 17β-hydroxyl group. After deprotecting the ketone group at position 3, compounds according to the invention are obtained: 17α-hydrocarbyl-17β-hydroxy-18-aminophenyl-oestr-4-en-3-ones.

To prepare compounds according to the invention having a double bond between the carbon atoms at positions 9 and 10, the 11-hydroxy-18-aminophenyl-oestr-5-ene-3,17-dione 3,17-diethyleneacetal or another 3,17-di-acetal is first converted into the corresponding 11β-alkane sulphonic acid ester by reaction with the corresponding alkanesulphonyl chloride. The sulphonic acid ester is then converted into the 18-aminophenyl-oestr-5,9(11)-diene-3,17-dione 3,17-diethyleneacetal. After deprotecting the positions 3 and 17, the 18-aminophenyl-oestra-4,9-diene-3,17-dione is obtained. After the ketone group at 3 has been reprotected by the formation of the corresponding 5(10),9(11)-diene-3,17-dione 3-ethyleneacetal or another 3-acetal, the required hydrocarbon group is introduced at position 17α with the simultaneous formation of a hydroxyl group at position 17β. After deprotecting the ketone group at position 3, compounds according to the invention are obtained: 17α-hydrocarbyl-17β-hydroxy-18-aminophenyl-oestra-4,9-dien-3-ones.

Where aminophenyl has been mentioned above, aminophenyl groups having the formula

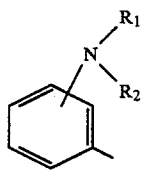

are meant, $R_1$ and $R_2$ having the meaning already described.

Esterification of the 17β-hydroxyl group of the compounds according to the invention thus prepared can be carried out in a manner known per se by reaction with the corresponding organic carboxylic acid or a functional derivative thereof such as the halide or the anhydride.

Etherification of the 17β-hydroxyl group of the compounds obtained may also be carried out by known methods through reaction with an alkyl halide in the presence of a base or in the presence of NaH in dimethylsulphoxide or tetrahydrofuran or through reaction with dihydropyrane in the presence of p-toluenesulfonic acid in a suitable solvent such as tetrahydrofuran.

Compounds according to the invention in which $R_3$ and $R_4$ represent a heterocyclic ring system containing O can also be prepared by methods known per se. See, for example, European Patent Application No. 116,974 and Tetrahedron Letters 10(1978), 883.

From the above it is clear that the preparation of a compound according to the present invention is characterized in that a corresponding compound having a protected ketone group at position 3 and, optionally, at position 17 of the steroid skeleton is deprotected and that, if desired and if present, the 17β-OH group is esterified or etherified or the 17-O group is converted to a heterocyclic ring system containing O. In the said corresponding compound the double bond(s) may be in another position than $\Delta^4$ and $\Delta^9$. Other positions may be $\Delta^{5(10)}$; $\Delta^5$; $\Delta^3$ and $\Delta^5$; $\Delta^{5(10)}$ and $\Delta^{9(11)}$. The position of these double bonds depends on the nature of the 3-O protecting group and is obvious to those skilled in the art.

The compounds according to the invention are compounds with a good pregnancy-terminating and/or pregnancy-preventing activity and a very low to zero antiglucocorticoid activity. Said compounds, and pharmaceutical products which contain one or more of said compounds as an active ingredient, may therefore very expediently be used as a pregnancy-terminating and/or pregnancy-preventing agent, it being possible to limit or avoid the side effects which are associated with antiglucocorticoid activity.

The invention is explained on the basis of the following examples.

EXAMPLE 1

5.3 g of magnesium shavings were suspended in 42 ml of dry tetrahydrofuran. A solution of 36.1 g of 3-bromodimethylaniline in 70 ml of dry tetrahydrofuran was then slowly added dropwise while stirring thoroughly in a nitrogen atmosphere. The reaction was started by adding a few drops of 1,2-dibromoethane. The reaction mixture was then stirred for 1.25 hours at reflux temperature. After cooling to +10° C., a solution of 28.0 g of 3,17-dioxo-oestr-5-ene-18,11β-lactone 3,17-diethyleneacetal in 140 ml of dry tetrahydrofuran was added dropwise.

After stirring for two hours at room temperature, the reaction mixture was cooled to 0° C. and then carefully decomposed with a solution of 36.4 g of ammonium chloride in 195 ml of water.

Extraction with ethyl acetate yielded an organic layer which was washed neutrally with a saturated solution of sodium chloride, dried over sodium sulphate, filtered, and concentrated by evaporation in vacuo.

After purifying by chromatography through silica gel, 35.6 g of crude 11β-hydroxy-18-(3-dimethylaminophenyl)oestr-5-ene-3,17,18-trione 3,17-diethyleneacetal were obtained. Crystallization from ethyl acetate yielded 30.2 g of pure substance. Melting point 172.4° C.; $[\alpha]_D^{20} = +71.8°$ (c=1% dioxane).

EXAMPLE II

In a similar manner the corresponding 18-(4-dimethylaminophenyl) compound was obtained from the 18,11β-lactone and 4-dimethylaminophenylmagnesium bromide. Melting point 233° C.; $[\alpha]_D^{20} = -29.2°$ (c=1%, chloroform)

EXAMPLE III

A solution of 132.2 ml of hydrazine hydrate and 23.3 ml of concentrated hydrochloric acid in 225 ml of triethylene glycol was added to a suspension of 41.3 g of 11β-hydroxy-18-(3-dimethyl-aminophenyl)-oestr-5-ene-3,17,18-trione 3,17-diethyleneacetal in 225 ml of triethylene glycol while stirring thoroughly in a nitrogen atmosphere. After stirring the reaction mixture for 1 hour at reflux temperature (130° C.), a solution of 58.9 g of potassium hydroxide in 60 ml of water was carefully added dropwise. The reaction mixture was now brought to 160° C. while simultaneously distilling off the lower boiling fractions. 63 ml of dimethyl sulphoxide was added at a temperature of +130° C. After stirring for 30 minutes at +160° C., the reaction mixture was cooled to room temperature and poured out into 4 liters of ice water. The precipitate was filtered off, washed neutrally with water and dried in vacuo. The 35.7 g of crude 11β-hydroxy-18-(3-dimethylaminophenyl)-oestr-5-ene-3,17-dione 3,17-diethyleneacetal thus obtained were crystallized from methylene chloride/ether. 33.8 g of pure diacetal was obtained. Melting point 194.8° C.; $[\alpha]_D^{20} = -4.9°$ (c=1%, dioxane).

EXAMPLE IV

In a similar manner, 11β-hydroxy-18-(4-dimethylaminophenyl)oestr-5-ene-3,17-dione 3,17-diethyleneacetal was obtained from 11β-hydroxy-18-(4-dimethylaminophenyl)-oestr-5-ene-3,17,18-trione 3,17-diethyleneacetal after reduction. Melting point 234.5° C.; $[\alpha]_D^{20} = +8.7°$ (c=1%, chloroform).

EXAMPLE V (a) 22.1 g of dicyclohexylcarbodiimide and 6.8 ml of dry pyridine were added to a solution of 17 g of 11β-hydroxy-18-(3-dimethylaminophenyl)oestr-5-ene-3,17-dione 3,17-diethyleneacetal in 60 ml of dry dimethyl sulphoxide and 60 ml of dry toluene at room temperature while stirring thoroughly in a nitrogen atmosphere. This solution was now cooled to +5° C. and 3.4 ml of dichloroacetic acid was then added dropwise at a temperature of <+20° C. After stirring for 45 minutes at room temperature, the reaction mixture was decomposed by adding 3.4 ml of methanol followed by a solution of 6.8 g of oxalic acid dihydrate in 55 ml of methanol.

After diluting the mixture with 120 ml of dry ether, the precipitate was filtered and rinsed well with dry ether. The filtrate was washed with a saturated sodium bicarbonate solution and water and dried over sodium sulphate, filtered and concentrated by evaporation in vacuo.

After purification by chromatography through silica gel, 13.7 g of 18-(3-dimethylaminophenyl)oestr-5-ene-3,11,17-trione 3,17-diethyleneacetal was obtained. Melting point 181.8° C.; $[\alpha]_D^{20} = +20.6°$ (c=1%, dioxane).

(b) In an analogous manner to that described in Example III, 18-(3-dimethylaminophenyl)oestr-5-ene-3,17-dione 3,17-diethyleneacetal was obtained from 18-(3-dimethylaminophenyl)oestr-5-ene-3,11,17-trione 3,17-diethyleneacetal after reduction. Melting point 180° C.; $[\alpha]_D^{20} = -34.3°$ (c=1%, dioxane).

(c) 10 ml of 2M hydrochloric acid was added to a solution of 3.7 g of 18-(3-dimethylaminophenyl)-oestr-5-ene-3,17-dione 3,17 diethyleneacetal in 180 ml of acetone. After stirring thoroughly for 30 minutes at reflux temperature in a nitrogen atmosphere, the reaction mixture was cooled to room temperature, neutralised with a saturated sodium carbonate solution, and then poured into 1.8 L of ice water. Extraction with methylene dichloride gave an organic layer which was given a neutral wash with water, dried over sodium sulphate, filtered and concentrated by evaporation in vacuo. The raw product was purified by chromatography through silica gel. Yield: 2.5 g (amorphous) 18-(3-dimethylaminophenyl)oestr-4-ene-3,17-dione; $[\alpha]_D^{20} = +109°$ (c=1%, dioxane).

(d) 2.0 ml of trietyl orthoformate and 9 mg of p-toluene-sulphonic acid were added consecutively at 0°-5° C. to a cold suspension of 2.4 g of 18-(3-dimethylaminophenyl)-oestr-4-ene-3,17-dione in 55 ml of 100% ethanol. After stirring for 2.75 hours at room temperature, the reaction mixture was neutralized by adding triethylamine and then pouring out into 600 ml of ice water. The precipitate was filtered off, washed neutrally with water and dried in vacuo. Yield: 2.5 g of 3-hydroxy-18-(3-dimethylaminophenyl)-oestr-3,5-dien-17-one 3-ethyl ether.

(e) The crude 3-hydroxy-18-(3-dimethylaminophenyl)-oestra-3,5-dien-17-one 3-ethyl ether thus obtained was dissolved in 40 ml of dry tetrahydrofuran and added dropwise at room temperature to a solution of allylmagnesium bromide in dry ether while stirring well in a nitrogen atmosphere.

The Grignard solution was prepared from 0.7 g of magnesium, 15 ml of dry ether and 1.4 ml of allylbromide.

The reaction mixture was stirred well for 1 hour at room temperature, then cooled to 0° C. and carefully decomposed with 3.5 ml of a saturated ammonium chloride solution (t<+10° C.).

Extraction with ethylacetate yielded an organic layer which was given a neutral wash with a saturated sodium chloride solution, dried over sodium sulphate, filtered and concentrated by evaporation in vacuo.

The crude Grignard product was dissolved in 15 ml of acetone. 0.5 ml of concentrated hydrochloric acid and 0.5 ml of water was added to this solution at room temperature while stirring well in a nitrogen atmosphere.

After stirring for 45 minutes at room temperature, the reaction mixture was poured out into 500 ml of ice water and neutralized with a saturated sodium bicarbonate solution.

The precipitate was filtered off, given a neutral wash with water, taken up in methylene dichloride and concentrated by evaporation in vacuo. After purification by chromatography through silica gel followed by crystallization from ether, 1.3 g of pure 17α-allyl-17β-hydroxy-18-(3-dimethylaminophenyl)oestr-4-en-3-one was obtained.

Melting point 141.9° C.; $[\alpha]_D^{20} = +46.4°$ (c=1% dioxane).

EXAMPLE VI

In the manner as described in Example V, pure 17α-allyl-17β-hydroxy-18-(4-dimethylaminophenyl)oestr-4-en-3-one was obtained from 11β-hydroxy-18-(4-dimethylaminophenyl)oestr-5-ene-3,17-dione 3,17-diethyleneacetal. Melting point 134.5° C.

EXAMPLE VII (a) 50.4 ml of methanesulphonyl chloride was added while stirring at 0° C. to a solution of 21.9 g of 11β-hydroxy-18(3-dimethylaminophenyl)oestr-5-ene-3,17-dione 3,17-diethyleneacetal in 215 ml of dry pyridine.

After stirring for 5 hours at 0° C., the reaction mixture was poured out into 500 ml of saturated sodium bicarbonate solution.

The precipitate was filtered off, washed with water and then taken up in methylene dichloride. The organic layer was dried over sodium sulphate, filtered and concentrated by evaporation in vacuo.

(b) The product (26.5 g) thus obtained was dissolved in 200 ml of dry pyridine.

After stirring for 1.5 hours at 100° C., the reaction mixture was cooled to room temperature and poured out into 2 L of water.

Extraction with methylene dichloride yielded an organic layer which was given a neutral wash with water, dried over sodium sulphate, filtered and concentrated by evaporation in vacuo.

After purification by chromatography through silica gel, 16.4 g of 18-(3-dimethylaminophenyl)oestr-5,9(11)-diene-3,17-dione 3,17-diethyleneacetal was obtained.

Melting point: 68° C.; $[\alpha]_D^{20} = -67.70°$ (c=1%, dioxane).

(c) 28 ml of water and 28 ml of 2M hydrochloric acid were added to a solution of 16.4 g of 18-(3-dimethylaminophenyl)oestr-5,9(11)-diene-3,17-dione 3,17-diethyleneacetal in 350 ml of acetone.

After stirring for 1.5 hours at reflux temperature, the reaction mixture was cooled to room temperature and concentrated by evaporation in vacuo to a volume of 150 ml and then poured out into 500 ml of saturated sodium bicarbonate solution.

The precipitate was filtered off, given a neutral wash with water and taken up in methylene dichloride. The organic layer was dried over sodium sulphate, filtered and concentrated by evaporation in vacuo. After chromatography of the dry residue through silica gel, 13.7 g of crude 18-(3-dimethylaminophenyl)oestr-4,9-diene-3,17-dione was obtained.

After crystallization from hexane, the pure product was isolated.

Melting point: 65.5° C.; $[\alpha]_D^{20} = -78.1°$ (c=1%, dioxane).

(d) A solution of 4.7 g of 18-(3-dimethylaminophenyl)oestr-4,9-diene-3,17-dione and 2 g of p-toluenesulphonic acid in 45 ml of dry triethyl orthoformate was stirred at room temperature for 3.5 hours.

Working up of the reaction mixture by neutralization with a saturated sodium bicarbonate solution, extraction with methylene dichloride and purification by chromatography through silica gel yielded 4.7 g of 18-(3-dimethylaminophenyl)-oestr-5(10),9(11)-diene-3,17-dione 3-ethyleneacetal $[\alpha]_D^{20} = +149.3°$ (c=1%, dioxane).

(e) The 4.7 g of 18-(3-dimethylaminophenyl)-oestra-5(10),9(11)-diene-3,17-dione 3-ethyleneacetal thus obtained was dissolved in 45 ml dry tetrahydrofuran at room temperature while stirring well in a nitrogen atmosphere, and added dropwise to a solution of allyl-magnesium bromide in dry ether.

The Grignard solution was prepared from 1.38 g of magnesium, 35 ml of dry ether and 2.8 ml of allylbromide.

The reaction mixture with the ethyleneacetal was stirred well for 30 minutes at room temperature, then cooled to 0° C. and carefully decomposed with 50 ml of saturated ammonium chloride solution.

After working up by extraction with methylene dichloride, the crude Grignard product isolated was dissolved in 38 ml of acetone 3 ml of water and 3 ml of concentrated hydrochloric acid were added to this solution at room temperature while stirring in a nitrogen atmosphere.

After stirring for 5.5 hours at room temperature, the reaction mixture was poured out into 400 ml of ice water and neutralized with a saturated sodium bicarbonate solution. The precipitate was filtered off, given a neutral wash with water, taken up in methylene dichloride and concentrated by evaporation in vacuo. After purification by chromatography through silica gel, 2.1 g of pure amorphous 17α-allyl-17β-hydroxy-18-(3-dimethylaminophenyl)oestra-4,9-dien-3-one was obtained. $[\alpha]_D^{20} = -220.8°$ (c=0.5%, dioxane).

EXAMPLE VIII

In the manner as described in Example VII, pure amorphous 17α-allyl-17β-hydroxy-18-(4-dimethylaminophenyl)oestra-4,9-dien-3-one was obtained from 11β-hydroxy-18-(4-dimethylaminophenyl)oestr-5-ene-3,17-dione 3,17-diethyleneacetal; $[\alpha]_D^{20} = -204.5°$ (c=1%, chloroform).

EXAMPLE IX

In the manner as described in Tetrahedron Letters 10 (1978) 883 18(4-dimethylaminophenyl)-17-hydroxy-3-oxo-oestr-4-en-17-propionic acid-γ-lactone $[\alpha]_D^{20} = 31.9°$ (c=½%, dioxane), was obtained from 18-(4-dimethylaminophenyl)oestr-5(10)-en-3,17-dion-3-ethyleneacetal.

I claim:

1. 18-phenylsteroids from the oestrane series having the general formula:

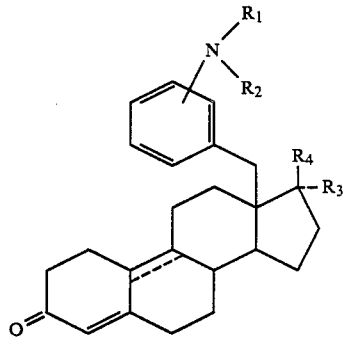

wherein

R₁ and R₂ each separately represent H or a (1–4 C) hydrocarbon radical or together represent a (2–6 C) hydrocarbon radical, R₃ represents H or a (1–4 C) hydrocarbon radical, optionally having an OH substituent, R₄ represents OH or an ester or ether group, or together with R₃ represents O or a heterocyclic ring system containing O, and wherein the broken line indicates an optionally present double bond between the carbon atoms at position 9 and 10 of the skeleton.

2. Steroids according to claim 1, wherein R₃ is (2–3 C) hydrocarbon group, optionally having an OH substituent, and R₄ is OH.

3. Steroids according to claim 1, wherein R₁ is a saturated alkyl group containing 1–3 carbon atoms.

4. Steroids according to claim 1, wherein R₂ is a saturated alkyl group containing 1–3 carbon atoms.

* * * * *